United States Patent [19]

DeFreitas

[11] Patent Number: 4,492,760
[45] Date of Patent: Jan. 8, 1985

[54] HLA D TYPING ASSAY

[75] Inventor: Elaine C. DeFreitas, Villanova, Pa.

[73] Assignee: The Wistar Institute of Anatomy and Biology, Philadelphia, Pa.

[21] Appl. No.: 486,441

[22] Filed: Apr. 19, 1983

[51] Int. Cl.$^3$ ...................... G01N 33/50; C12N 15/00
[52] U.S. Cl. .................................. 436/503; 436/504; 436/804; 436/811; 436/823; 436/815; 435/4; 435/29; 435/35; 435/172.2; 435/174; 435/240; 435/948; 935/101; 935/110
[58] Field of Search ............... 436/503, 504, 518, 519, 436/543, 804, 815, 811, 823, 501; 435/2, 4, 21, 25, 28, 29, 35, 172, 948, 174; 23/915, 920, 240; 935/101, 110

[56] References Cited

U.S. PATENT DOCUMENTS

| | | | |
|---|---|---|---|
| 4,124,701 | 11/1978 | Bach et al. | 435/240 |
| 4,265,873 | 5/1981 | Sheehy et al. | 424/1.1 |
| 4,294,802 | 10/1981 | Johansson | 417/475 |
| 4,314,026 | 2/1982 | Descamps-Latscha | 422/52 |
| 4,318,886 | 3/1982 | Kawahara et al. | 356/39 |

OTHER PUBLICATIONS

Kearns, R. J. et al., Federation Proceedings; FASEB, vol. 39, (3), p. 355, Abstract 449, (1980).
Skidmore, B. J. et al., Federation Proceedings; FASEB, vol. 39, (3), p. 936, Abstract 3517, (1980).
DeFreitas, E. et al., Federation Proceedings; FASEB, vol. 39, (3), p. 944, Abstract 3554, (1980).
Rosenthal, A. S. et al., *Immunology* 80, eds. Fougereau, M. & Dauesset, J., p. 458, Academic Press, London, (1980).
DeFreitas et al., (1982), *Current Topics in Microbiology and Immunology*, 100: 191-201.
Foundation Marcell Merieux, Abstract Book, Sixth International Conference on Tetanus, (Lycon, France, Dec. 3-5, 1981).
Maizel et al., (1982), *Proceeding of the National Academy of Sciences USA*, 79: 5998-6002.
Mayer et al., (1982), *Journal of Experimental Medicine*, 156: 1860-1865.
Butler et al., (1983), *Journal of Experimental Medicine*, 157: 60-68.
Lakow et al., (1983), *Journal of Immunology*, 130: 169-172.
Foung et al., (1982), *Proceedings of the National Academy of Sciences USA*, 79: 7484-7488.
Green et al., (1982), *Journal of Immunology*, 129: 1986-1992.
Kobayashi et al., (1982), *Journal of Immunology*, 128, 2714-2718.
Okata et al., (1981), *Proceedings of the National Academy of Sciences USA*, 78: 7717-7721.
Irigoyen et al., (1981), *Journal of Experimental Medicine*, 154: 1827-1837.
Grillot-Courvaline et al., (1981), *Nature*, 292: 844-845.
DeFreitas et al., (1982), *Proceedings of the National Academy of Sciences USA*, 79: 6646-6650.
Fox, *Chemical & Engineering News*, pp. 15-17, (Jan. 1, 1979).

*Primary Examiner*—Benjamin R. Padgett
*Assistant Examiner*—M. Moskowitz
*Attorney, Agent, or Firm*—Banner, Birch, McKie & Beckett

[57] ABSTRACT

An assay for HLA D phenotype wherein antigen-pulsed monocytes are contacted with antigen-specific T lymphocytes or T cell hybridomas and the extent of selective binding between the pulsed monocytes and the T lymphocytes or T cell hybridomas determines HLA D phenotype of the monocyte. The assay is particularly useful for quickly typing donor tissue prior to transplantation.

36 Claims, No Drawings

HLA D TYPING ASSAY

TECHNICAL FIELD

The present invention is directed to a method of determining HLA D type.

BACKGROUND OF THE INVENTION

In man, responses to HLA antigens dominate the strong immunological reaction to transplanted tissue. In order to avoid rejection of transplanted tissue, it is desirable to match donor HLA type to the recipient HLA type. The HLA type of an individual is determined by antigens encoded by genes on a single chromosome. Four principal HLA antigen loci have been identified on chromosome six and have been designated A, B, C and D (and the closely-related DR locus). The major lymphocyte activating determinants are controlled by alleles at the forth locus, D. The matching of recipient and donor D allotypes has proved to be a major factor in reducing transplant rejection and transfusion reaction. This is most likely attributable to the fact that cytotoxic T lymphocytes against HLA A and B antigens are generated by D locus differences.

Typing of the D locus is typically carried out in a one-way mixed lymphocyte reaction (MLR). In a MLR, two groups of genetically dissimilar lymphocytes are cultured together. One of the populations (stimulators) has been made immunologically unresponsive by treatment with radiation or Mitomycin C. The other cell population responds to the phenotypically dissimilar determinants on the surface of the irradiated cell population. To conduct a typing assay employing MLR, a screening panel of donors with known HLA D types is required as stimulators. This panel of homozygous typing cells are best found in families of cousin marriages. The unknown donor's PBL are cultured individually with the typing panel for five to seven days. If the unknown donor's HLA D allotype is different than the allotype of the screening lymphocyte, there will be an immunological response by the donor's PBL. The unknown donor's allotype will be indicated, therefore, by nonreactivity in the culture containing the stimulating lymphocytes of identical HLA D type.

Another method employed to determine HLA D type is the mixed lymphocyte cytotoxcity test (MLC). The first phase of the MLC requires the stimulating of the donor's lymphocytes with a screening panel as described above for the MLR (5-7 days). Responding primed lymphocytes are harvested and assayed for cytotoxcity on a panel of B lymphoblastoid cell lines with known HLA D types. These target cells have been prelabeled with a radioisotope. Donor lymphocytes from the first phase, which have been primed to a foreign HLA D type, will kill the radiolabeled targets with the same D type to which they have been primed. Cytotoxic reaction can be detected by radioactivity in the supernatant. This assay requires an additional 6 to 8 hours after the MLR phase.

While the above methods are accurate to determine HLA D type, the lengthy procedures involved are unsuitable for typing donors and recipients for transplant procedures. Generally, the donor is a cadaver and it is necessary to transplant the organ as quickly as possible (e.g., within 24 hours). A need, therefore, exists for an expedient test for HLA D type.

SUMMARY OF THE INVENTION

It is an object of the present invention to provide an assay that determines the HLA D type of human monocytes.

It is another object of the present invention to provide an assay that expediently determines HLA D type.

It is a further object of the present invention to provide an assay that can quickly match donor and recipient HLA D types for tissue transplants.

A still further object of the present invention is to provide an assay for HLA D type that employs human T cell hybridomas.

Yet another object of the present invention is to provide an assay that can determine whether a human T cell hybridoma is antigen-specific.

These and other objects of the present invention are provided by a method comprising (a) pulsing human monocytes with a particular antigen; (b) contacting said pulsed monocytes with at least one screening cell culture selected from the group consisting of antigen-specific T lymphocytes and antigen-specific T cell hybridomas, the cells in each said screening cell culture being substantially of a single HLA D binding type and specific for said particular antigen; and (c) determining whether said pulsed monocytes selectively bind to said screening cells.

DETAILED DESCRIPTION OF THE PREFERRED EMBODIMENT

The present invention is directed to a novel assay which can quickly and reliably determine the HLA D type of an individual by culturing antigen-pulsed monocytes obtained from the individual with a culture of antigen-specific screening cells that are either T lymphocytes or T cell hybridomas. The present assay can also be employed to determine whether a T cell hybridoma is antigen-specific. The present invention takes advantage of the fact that antigen-specific T lymphocytes or T cell hybridomas will bind selectively to antigen-pulsed monocytes that are of the same HLA D "binding type" as the screening cells.

The present invention further takes advantage of immortal T cell hybridomas that retain antigen-specificity such as those disclosed in copending application Ser. No. 486,439, entitled "Human T Cell Hybridomas" filed on even date herewith, the disclosure of which is expressly incorporated by reference herein. Several unique advantages, previously unavailable, are achieved by the present invention. First, easily maintained immortal T cell hybridomas are available as a permanent source of cells for screening monocytes of unknown HLA D type. Of course, other continuous, antigen-specific T lymphocytes of defined HLA D type would be advantageous if available. Second, the assay can be accomplished in a matter of a few hours, which is of great importance when a donor cadaver must be matched to a recipient prior to a transplant.

The HLA D locus antigens are closely related to the HLA DR antigens. It is believed by some investigators that D and DR are, in fact, the same locus. The D and DR loci, at a minimum, appear to be very closely linked on the chromosome. The uncertainty arises in that D antigens are defined by antigen-specific lymphocytes, while DR antigens are defined by antibodies. It has not, therefore, been determined conclusively whether the antigenic sites for D and DR are identical. Since the method of the present invention employs T lymphocytes or T cell hybridoma to determine antigen type, the phenotype determined shall be referred to herein as the HLA D type. It is understood, however, that the present invention may define HLA DR as well.

The assay disclosed herein can employ either T lymphocytes or T cell hybridomas that bind to antigen-pulsed monocytes. The preferred cells are helper T lymphocytes and T cell hybridomas wherein one of the parent cells in a helper T lymphocyte. For simplicity, the invention will be described in terms of the T cell hybridoma embodiment. It should be understood, however, that a helper T lymphocyte could be readily employed in the same manner as the T cell hybridomas described below.

According to the preferred embodiment of the present invention, human T cell hybridomas are employed to determine the HLA D phenotype of monocytes. The hybridomas should express antigen-specificity. That is, the hybridomas should selectively bind monocytes pulsed with only one particular antigen. For example, a hybridoma specific for tetanus toxoid will selectively bind monocytes that have been pulsed with tetanus toxoid as opposed to monocytes that have not been pulsed with tetanus or that have been pulsed with an unrelated antigen. The preferred hybridomas employed in the present invention are those described more fully in copending application Ser. No. 486,439, entitled "Human T Cell Hybridomas," filed on even date herewith. Such hybridomas are the progeny (i.e., clonally derived from) a somatic cell hybrid formed by fusing a human lymphoma cell and an antigen-specific T lymphocyte, such as a helper T lymphocyte. The preferred hybridomas for the assay are those derived from a human lymphoma cell of T lymphocyte origin and an antigen-specific helper T lymphocyte.

Methods of isolating antigen-specific T lymphocytes are known in the art. See Kurnick, et al., (1979) J. Immunol. 122: 1255–1260. Human lymphoma cell lines of T lymphocyte origin are also known in the art. The preferred parent lymphoma is a selectable-mutant derived from the human lymphoma cell line Jurkat as disclosed in copending application Ser. No. 486,440, entitled "Human Lymphoma Cell Lines Suitable for Hybridization," filed on even date herewith, the disclosure of which is expressly incorporated by reference herein. The Jurket cell line is a Sezary T cell lymphoma, has 46 chromosomes and is XY. It exhibits a phenotype of sheep erythrocyte receptor-positive, OKT3 antigen-positive, Fc receptor-positive, OKT4 and OKT8-positive (variable), and surface Ig-negative. It also produces Il-2 after stimulation with concavalin A and phytohemagglutinin. A cell "derived from" this cell line would be a clone of the cell line or a mutant clone of the cell line.

Two cell lines suitable for hybridization were deposited with the American Type Culture Collection (ATCC), 12301 Parklawn Drive, Rockville, Md. 20852, on Mar. 11, 1983. One suitable selectable-mutant derived from the Jurkat cell line is under ATCC Deposit No. CRL-8226. The other selectable mutant, cured of PPLO, is under ATCC Deposit No. CRL-8224. These selectable-mutants are hypoxanthine phosphoribosyltransferase(HPRT)-negative and, therefore, sensitive to media containing hypoxanthine, aminopterin and thymidine (HAT).

The basic process of producing hybridomas is well known in the art. See, e.g., *Monoclonal Antibodies* (R. Kennett, T. McKeran and K. Bechtol eds. 1980). A particularly preferred method is disclosed by Kontianen, et al., (1978) *Nature* 274: 477–480. Generally, the process as applied in the present invention comprises pelleting normal antigen-specific human helper T lymphocytes and HAT-sensitive human lymphoma cells together in a ratio of approximately 5-to-1, respectively. The pelletized cells are then suspended in a 50% solution of polyethylene glycol in serum-free RPMI 1640. Prewarmed RPMI 1640 is then slowly added, the cells repelleted, and then suspended in RPMI 1640, 15% fetal calf serum, and HAT-containing media. Cell cultures are fed fresh HAT media weekly. After approximately one to two weeks, unfused T lymphocytes and lymphoma cells die.

Successful cell hybrids can generally be observed by seven weeks after fusion. Hybridomas recovered should then be cloned for one to four months at which point the chromosome number should stabilize as well as the antigen-specific phenotypes. A modification of the assay disclosed herein can then be used to determine whether the hybridomas retain antigen-specificity. "Antigen-specific" or "antigen specificity" refers to the ability of the T cell hybridoma or T lymphocyte to selectively bind monocytes pulsed with only one particular antigen. If there is selective binding, the hybridoma or lymphocyte is "specific" for that antigen.

There are currently believed to be twelve HLA D allotypes important to tissue transplantation, although more may be characterized in the future. To employ antigen-specific T cell hybridomas or T lymphocytes as "screening cells" in the present invention, therefore, it is necessary to determine the screening cells' "binding type," i.e., the D allotype the screening cells selectively recognize when binding antigen-pulsed monocytes.

T lymphocytes are often heterozygous and T cell hybridomas can express even more than two HLA D phenotypes. Only one of the allotypes, however, is determinative of antigen-specific binding of the screening cells to the antigen-pulsed monocytes. Thus, while a hybridoma may bind to, for example, three different D allotypes expressed by monocytes when those monocytes have not been antigen-pulsed, if the monocytes are antigen-pulsed, the hybridoma will selectively recognize only one allotype. While not wishing to be bound by this theory, applicant believes that this is due to a very close association of the antigen and HLA D recognition sites on T lymphocytes or their hybridomas. This phenomenon is not observed in monocytes, however. A heterozygous monocyte can selectively bind to T lymphocytes or hybridomas that have a "binding type" identical to either of the monocyte allotypes since each of the allotypes are expressed on the monocytes' surface.

In the preferred embodiment, therefore, the assay employs twelve stock T lymphocyte or T cell hybridoma screening cultures each of which exhibits antigen-specific binding for a different HLA D allotype (i.e., different "binding types"). If selective binding is observed in only one culture, the monocytes are homozygous for that screening culture's "binding type." If two screening cultures show selective binding, the monocytes are heterozygous.

Generally, the actual assay of the present invention involves culturing antigen-pulsed monocytes with T cell hybridomas of a known HLA D binding type that are specific for the antigen pulsed to the monocyte. When the object of the assay is to determine the HLA D type of a potential transplant donor or recipient, the typical procedure would comprise obtaining a sample of peripheral blood lymphocytes (PBL) from the donor or recipient, and exposing the PBL to gamma radiation to prevent an immunological response to the screening culture by the PBL. Among the PBL will be monocytes. The irradiated PBL are then pulsed (i.e., contacted with) the antigen for which the screening T cell hybridomas are specific for two to three hours The pulsed PBL are then added to the various screening cultures. After incubating the antigen-pulsed PBL and screening cultures together, the HLA D type of the PBL will be readily apparent by determining in which screening culture(s) the PBL and screening cells selectively bind.

While other methods of determining selective binding between antigen-pulsed PBL (or monocytes) and a screening culture of T lymphocytes or T cell hybridomas could be employed (e.g., microscopic determination), the preferred method is to radiolabel the T lymphocyte or T cell hybridoma screening cultures and then culture the screening cells with antigen-pulsed monocytes attached to a solid support. Nonadherent cells can then easily be washed away, the adherent cells detached from the solid support and the relative extent of T lymphocyte or T cell hybridoma binding determined by liquid scintillation counting. T lymphocytes or T cell hybridomas can easily be radiolabeled by culturing the cells overnight in a medium containing $^3$H-TdR. Screening cultures can also be enzyme labeled by techniques well known in the art. An ELISA assay can then be employed if radiolabeling is not convenient.

Monocytes can be adhered to solid support, such as glass, plastic, etc., by merely allowing a suspension of the monocytes to contact the support for several hours. Preferred solid support is a polystyrene microtiter plate. The monocytes can be detached from solid supports by treatment with a solution containing trypsin and 0.1M EDTA in isotonic saline.

The following examples are included for illustrative purposes only and are in no way intended to limit the scope of the invention.

EXAMPLE I

The following example demonstrates antigen-specific binding by T cell hybridomas to antigen-pulsed monocytes of only one HLA D allotype.

A T cell hybridoma was prepared according to the method disclosed in copending application entitled "Human T Cell Hybridomas," Ser. No. 486,439, filed on even date herewith. The hybridoma, designated SH2, is specific for tetanus toxoid antigen. The DR-type of the hybridomas is 2/4/7, as established by DR-specific alloantisera. A subclone of SH2, designated SH2E6, was deposited with the ATCC on Mar. 11, 1983 under Deposit No. HB-8225.

The hybridomas were first harvested from a T-75 flask containing tetanus toxoid. The cells were washed two times in sterile saline and resuspended in fresh RPMI 1640 containing fetal calf serum and 2 uCi/ml $^3$H-TdR at a concentration of $5 \times 10^5$ cells/ml. The cells were then placed in a new T-75 flask and incubated overnight at 37° C. and 5% $CO_2$. The next morning, the cells were harvested and washed twice in sterile saline before being resuspended in fresh media at $1 \times 10^6$ cells/ml.

The day of the assay, 20 ml of blood was withdrawn from five patients. DR-typing with specific alloantisera indicated that the various donors had the following DR types: 7/2, 5/2, 2/2, 5/5 and 3/4. PBL was separated from the blood samples by density centrifugation using commercial Lymphoprep (Nyeguard, Oslo, Norway). The PBL was then washed twice in sterile saline, irradiated with 4000 R and resuspended in fresh media containing 20% human AB serum at a concentration of $10 \times 10^6$ cells/ml.

Into a 96-well microtiter plate (Costar, Cambridge, Mass.) were seeded approximately 100 ul/well of the PBL suspension. Tetanus toxoid was added to 48 wells to final concentration of 100 ug/ml. To all of the wells was added 100 ul of the final suspension of hybridomas described above. The plates were incubated for three hours at approximately 37° C. in 5% $CO_2$. To remove nonadherent cells, the plates were gently washed by three rounds of aspirations and additions of warm (37° C.) sterile saline. Then 200 ul of saline solution containing 0.01M EDTA 0.25% (w/v) trypsin was added to the wells and allowed to incubate for 15 minutes at 37° C. to detach adherent cells. The contents of all the wells were harvested by an automatic cell harvester onto glass fiber discs. The discs were then counted in a liquid scintillation counter.

Table 1 shows the number of hybridomas that bound to various monocytes pulsed with tetanus toxoid. The data indicates that the hybridoma has a "binding type" of D2 (assuming D-type is equivalent to DR-type). When neither of the monocytes' allotype was DR2, significantly less binding occurred. The data clearly shows selective binding for D2. Table 2 shows binding between the hybridomas and monocytes that were not antigen-pulsed. It is clear that there was some selective binding for monocytes of type 7. The binding was not, however, as selective as when the monocytes were antigen-pulsed.

TABLE 1

| Monocyte DR type* | Number of Tet-specific T—T hybrids Bound to Monocytes Prepulsed with ⁻ | |
|---|---|---|
| | media ⁼ | Tet |
| 7/2 | 6,313 | 11,582 |
| 5/2 | 6,221 | 13,071 |
| 2/2 | 5,548 | 6,959 |
| 5/5 | 1,612 | 2,664 |
| 3/4 | 2,652 | 2,739 |

*Typed with DR-specific alloantisera.
⁺ 50,000 T—T hybrids, pre-labeled with $^3$H—TdR, were added to monolayers of 40–50 × 10$^3$ monocytes prepulsed with nothing (media) or 100 ug/ml Tet.
⁻ SEM 10% of the mean.

TABLE 2

| Monocyte DR type* | Number of Tet-specific T—T hybrids Bound to Monocytes ⁻ |
|---|---|
| 7/1 | 8,121 |
| 7/7 | 5,050 |
| 7/3 | 6,001 |
| 7/3 | 5,484 |
| 7/2 | 6,313 |
| 5/5 | 1,612 |
| 3/4 | 2,652 |

*Typed with DR-specific alloantisera.
⁻ 50,000 T—T hybrids, pre-labeled with $^3$H—TdR, were added to monolayers of 40–50 × 10$^3$ monocytes. SEM less than 10% of the mean.

EXAMPLE II

The following exemplifies the use of the assay in the present invention to determine whether a particular hybridoma is antigen-specific.

Hybridomas disclosed in copending patent application Ser. No. 486,439, entitled "Human T Cell Hybridomas" filed on even date herewith, were tested for tetanus toxoid specificity. The T cell hybridomas and Jurkat-6-TG-3 cells were prelabeled with one 1 uCi/ml $^3$H-TdR in RPMI 1640 and 15% fetal calf serum overnight at 37° C. The cells were then extensively washed, counted and equal numbers added to microtiter plates. The plates also contained gamma-irradiated (4000 R) adherent cells from a suspension of $5 \times 10^5$ PBL that was autologous to the normal T lymphocyte parent of the hybridomas. The adherent cells had been pulsed previously for three hours at 37° C. with either nothing, tetanus toxoid at 20 ug/ml, or SKSD at 20 ug/ml. The labeled lymphocytes were allowed to incubate for three hours at 37° after which nonadherent cells were washed away. Adherent cells were detached with 0.25 (w/v) trypsin in a 0.1M aqueous solution of EDTA and harvested onto glass fiber paper with the titertek. The filters were then dried and counted in a liquid scintillation cocktail. Greater than 50% of SH2 bound to antologous monocytes prepulsed with tetanus, while only 1-2% of the Jurkat-6-TG-3 bound in the presence or absence of tetanus. Less than 1% of the hybridomas attached to wells without monocytes or to empty wells pulsed with tetanus toxoid alone. The results are shown in Table 3.

TABLE 3

Recognition of Tet by human T—T hybrids: binding of hybrids to antigen-pulsed autologous monocytes.
Binding to autologous monocytes prepulsed with:+

| Hybrids tested | Media | Tet | SKSD |
| --- | --- | --- | --- |
| SH1 | 564 (13%) | 1,097 (26%) | 604 (14%) |
| SH2 | 500 (12%) | 2,386 (57%) | 469 (11%) |
| SH3 | 429 (13%) | 814 (26%) | 405 (13%) |
| SH5 | 325 (7%) | 298 (7%) | 216 (5%) |
| Jurkat 6-TG-3 (parent) | 108 (1%) ) | 292 (2%) | 146 (1%) |

+The results are expressed as mean cmp of $^3$H—TdR collected on filter strips from the cells binding to the adherent cell population. SEM was greater than 10% of the mean. Number in parentheses is percentage of T cells that adhered to the attached monocytes out of the total number added to the adherent cell monolayer.

The above examples are specific embodiments of the present invention. Variations will readily occur to those of skill in the art. The invention, therefore, is limited only by the scope of the appended claims.

I claim:

1. A method of determining the HLA D type of human monocytes comprising:
   (a) pulsing human monocytes with a particular antigen;
   (b) contacting said pulsed monocyte with at least one screening cell culture selected from the group consisting of antigen-specific T lymphocytes and antigen-specific T cell hybridomas, the cells in each said screening cell culture being substantially of a single HLA D binding type and specific for said particular antigen; and
   (c) determining whether said pulsed monocytes selectively bind to said screening cells.

2. The method of claim 1 wherein said pulsed monocytes are contacted with more than one screening culture of different HLA D binding types, the quantity of said pulsed monocytes contacted to each screening culture being approximately equal and each of said screening cultures having an approximately equal number of cells.

3. The method of claim 1 wherein said pulsed monocytes are attached to a solid support.

4. The method of claim 2 wherein said pulsed monocytes are attached to a solid support.

5. The method of claim 1 wherein said screening cultures are radiolabeled.

6. The method of claim 2 wherein said screening cultures are radiolabeled.

7. The method of claim 3 wherein said screening cultures are radiolabeled.

8. The method of claim 4 wherein said screening cultures are radiolabeled.

9. The method of claim 1 wherein said screening cultures are enzyme labeled.

10. The method of claim 2 wherein said screening cultures are enzyme labeled.

11. The method of claim 3 wherein said screening cultures are enzyme labeled.

12. The method of claim 4 wherein said screening cultures are enzyme labeled.

13. The method of claim 1 wherein said screening cultures are cultures of human T cell hybridomas cloned from a somatic cell hybrid of a first parent cell derived from a human lymphoma cell line and a second parent cell that is a normal, human T lymphocyte specific for said particular antigen.

14. The method of claim 2 wherein said screening cultures are cultures of human T cell hybridomas cloned from a somatic cell hybrid of a first parent cell derived from a human lymphoma cell line and a second parent cell that is a normal human T lymphocyte specific for said particular antigen.

15. The method of claim 3 wherein said screening cultures are cultures of human T cell hybridomas cloned from a somatic cell hybrid of a first parent cell derived from a human lymphoma cell line and a second parent cell that is a normal human T lymphocyte specific for said particular antigen.

16. The method of claim 4 wherein said screening cultures are cultures of human T cell hybridomas cloned from a somatic cell hybrid of a first parent cell derived from a human lymphoma cell line and a second parent cell that is a normal human T lymphocyte specific for said particular antigen.

17. The method of claim 5 wherein said screening cultures are cultures of human T cell hybridomas cloned with a somatic cell hybrid of a first parent cell derived from a human lymphoma cell line and a second parent cell that is a normal human T lymphocyte specific for said particular antigen.

18. The method of claim 6 wherein said screening cultures are cultures of human T cell hybridomas cloned from a somatic cell hybrid of a first parent cell derived from a human lymphoma cell line and a second parent cell that is a normal human T lymphocyte specific for said particular antigen.

19. The method of claim 7 wherein said screening cultures are cultures of human T cell hybridomas cloned from a somatic cell hybrid of a first parent cell derived from a human lymphoma cell line and a second parent cell that is a normal human T lymphocyte specific for said particular antigen.

20. The method of claim 8 wherein said screening cultures are cultures of human T cell hybridomas cloned from a somatic cell hybrid of a first parent cell derived from a human lymphoma cell line and a second parent cell that is a normal human T lymphocyte specific for said particular antigen.

21. The method of claim 9 wherein said screening cultures are cultures of human T cell hybridomas cloned from a somatic cell hybrid of a first parent cell derived from a human lymphoma cell line and a second parent cell that is a normal human T lymphocyte specific for said particular antigen.

22. The method of claim 10 wherein said screening cultures are cultures of human T cell hybridomas cloned from a somatic cell hybrid of a first parent cell derived from a human lymphoma cell line and a second parent cell that is a normal human T lymphocyte specific for said particular antigen.

23. The method of claim 11 wherein said screening cultures are cultures of human T cell hybridomas cloned from a somatic cell hybrid of a first parent cell derived from a human lymphoma cell line and a second parent cell that is a normal human T lymphocyte specific for said particular antigen.

24. The method of claim 12 wherein said screening cultures are cultures of human T cell hybridomas cloned from a somatic cell hybrid of a first parent cell derived from a human lymphoma cell line and a second parent cell that is a normal human T lymphocyte specific for said particular antigen.

25. The method of claim 13 wherein said first parent cell is derived from the human lymphoma cell line Jurkat.

26. The method of claim 14 wherein said first parent cell is derived from the human lymphoma cell line Jurkat.

27. The method of claim 15 wherein said first parent cell is derived from the human lymphoma cell line Jurkat.

28. The method of claim 16 wherein said first parent cell is derived from the human lymphoma cell line Jurkat.

29. The method of claim 17 wherein said first parent cell is derived from the human lymphoma cell line Jurkat.

30. The method of claim 18 wherein said first parent cell is derived from the human lymphoma cell line Jurkat.

31. The method of claim 19 wherein said first parent cell is derived from the human lymphoma cell line Jurkat.

32. The method of claim 20 wherein said first parent cell is derived from the human lymphoma cell line Jurkat.

33. The method of claim 21 wherein said first parent cell is derived from the human lymphoma cell line Jurkat.

34. The method of claim 22 wherein said first parent cell is derived from the human lymphoma cell line Jurkat.

35. The method of claim 23 wherein said first parent cell is derived from the human lymphoma cell line Jurkat.

36. The method of claim 24 wherein said first parent cell is derived from the human lymphoma cell line Jurkat.

* * * * *